US007465729B2

(12) United States Patent
Wessel et al.

(10) Patent No.: US 7,465,729 B2
(45) Date of Patent: Dec. 16, 2008

(54) METHODS OF TREATMENT OF MENOPAUSE AND PERIMENOPAUSE USING ESZOPICLONE

(75) Inventors: Thomas Wessel, Lenox, MA (US); Judy Caron, Westwood, MA (US)

(73) Assignee: Sepracor Inc., Marlborough, MA (US)

( * ) Notice: Subject to any disclaimer, the term of this patent is extended or adjusted under 35 U.S.C. 154(b) by 387 days.

(21) Appl. No.: 11/099,155

(22) Filed: Apr. 5, 2005

(65) Prior Publication Data
US 2005/0222157 A1 Oct. 6, 2005

Related U.S. Application Data

(60) Provisional application No. 60/559,590, filed on Apr. 5, 2004.

(51) Int. Cl.
*A61K 31/495* (2006.01)
(52) U.S. Cl. ..................................................... 514/249
(58) Field of Classification Search .................. 514/249; 424/45
See application file for complete search history.

(56) References Cited

U.S. PATENT DOCUMENTS 5,786,357 A * 7/1998 Young et al. ................. 514/249
6,153,216 A * 11/2000 Cordes et al. ............... 424/449

FOREIGN PATENT DOCUMENTS

WO WO 93/10787 6/1993

OTHER PUBLICATIONS

Soares et al. Six-month efficacy study of eszopiclone in perimenopausal and postmenopausal women with chronic insomnia. Obstetrics and Gynecology, Apr. 1, 2004, vol. 103, Suppl. No. 4 p. 102.*
Furukawa et al., "Antidepressant and benzodiazepine for major depression," John Wiley & Sons, Ltd., (1), 1-43, (2005).
Cohen, et al.; "Sleep in chronic pain: problems and treatments," Int'l Review of Psychiatry; vol. 12, No. 2: pp.115-126 (2000).
Drewes et al.; "Zopiclione as Night Medication in Rheumatoid Arthritis," Scand J Rheumatol; 27: 180-7 (1998).
Affleck G, Urrows S, Tennen H, Higgins P, Abeles M, *Seqeuntial daily relations of sleep, pain intensity, and attention to pain among women with fibromyalgia pain* 68:363-368 (1996).
Asnis GM, Chakrabarty A, DuBoff EA, et al; *Zolpidem for persistent insomnia in SSRI-treated depressed patients* J Clin Psychiastry 60:668-676 (1999).
Barone P, Amboni M., Vitale C, Bonavita V., *Treatment of nocturnal disturbance and excessive daytime sleepiness in Parkinson's disease*, Neurology 63:S35-S38 (2004).
Benca RM, Ancoli-Israel A, Moldofsky H., *Special considerations in insomnia diagnosis and management: Depressed, elderly, and chronic pain populations* J Clin Psychiatry 65 (Suppl 8):26-35 (2004).

Billiard M, Bentley A. *Is insomnia best categorized as a symptom or a disease?* Sleep Medicine 5(Suppl 1):S35-S40 (2004).
Bliwise DL, *Sleep disorders in Alzheimer's disease and other dementias*, Clin. Cornerstone 6 Suppl 1A:S16-28 (2004).
Bloom BJ, Owens JA, McGuinn M, Nobile C., Shaeffer L, Alario AJ, *Sleep and its relationship to pain, dysfunction, and disease activity in juvenile rheumatoid arthritis*; J Rheumatol 29:169-173 (2002).
Bourguignon C, Labyak SE, Taibi D, *Investigating sleep disturbances in adults with rheumatoid arthritis*, Holist Nurs Pract 17:241-249 (2003).
Breslau N, Roth T, Rosenthal L, Andreski P, *Sleep disturbance and psychiatric disorders: a longitudinal epidemiological study of young adults*, Biol Psychiatry 39:411-418 (1996).
Chang PP, Ford DE, Mead LA et al., *Insomnia in young men and subsequent depression. The Johns Hopkins Precursors Study*, Am J Epidemiol. 146:105-114 (1997).
Dorsey CM, Lee KA, Scharf MB *Effect of zolpidem on sleep in women with perimenopausal and postmenopausal insomnia: A 4-week, randomized, multicenter, double-blind placebo-controlled study* Clin Ther 16:873-897 (2004).
Drewes AM *Pain and sleep disturbances with special reference to fibromyalgia and rheumatoid arthritis*, Rheumatology (Oxford) 38:1035-1038 (1999).
Drewes AM, Nielsen KD, Hansen B, Taagholt SJ, Bjerregard K, Svendsen L, *A longitudinal study of clinical symptoms and sleep parameters in rheumatoid arthritis*, Rheumatology (Oxford) 39:1287-1289 (2000).
Drewes AM, Svendsen L, Taagholt, Bjerregard k, Nielsen KD, Hansen B, *Sleep in rheumatoid arthritis: a comparison with healthy subjects and studies of sleep/wake interactions*, Br J Rheumatol 37:71-81 (1998).
Ford DE, Kamerow DB, *Epidemiologic study of sleep disturbances and psychiatric disorders. An opportunity for prevention?*, JAMA 262:1479-1484 (1989).
Ford DE, Cooper-Patrick L, *Sleep disturbances and modd disorders:an epidemiologic perspective*, Depress Anxiety 14:3-6 (2001).
Gillin JC, *Are sleep disturbances risk factors for anxiety, depressive and addictive disorders?* Acta Psychiatr Scand Suppl. 393:39-43 (1998).
Hyyppa MT, Kronholm E, *Quality of sleep and chronic illnesses* J Clin Epidemiol 42:633-638 (1989).
Katz DA, McHorney CA. *Clinical correlates of insomnia in patients with chronic illness*. Arch Intern Med 158:1099-1107 (1998).
Koren D, Arnon I, Lavie P, et al. *Sleep complaints as early predictors of posttraumatic stress disorder: a 1-year prospective study of injured survivors of motor vehicle accidents*. Am J Psychiatry 159:855-857 (2002).
Livingston G, Blizard B, Mann A, *Does sleep disturbance predict depression in elderly people? A study in inner London*, Br J Gen Pract. 43:445-448 (1993).
Londborg PD, Smith WT, Glaudin V, Painter JR. *Short-term cotherapy with clonazepam and fluoxetine: anxiety, sleep disturbance and core symptoms of depression.*, J. Affect Disord. 61:73-79 (2000).

(Continued)

Primary Examiner—Jennifer Myong Kim
(74) Attorney, Agent, or Firm—Heslin Rothenberg Farley & Mesiti P.C.

(57) ABSTRACT

The invention relates to the use of eszopiclone for the treatment of symptoms accompanying perimenopause or menopause.

4 Claims, No Drawings

OTHER PUBLICATIONS

Mahowald MW, Mahowald ML, Bundlie SR, Ytterberg SR, *Sleep fragmentation in rheumatoid arthritis* Arthritis Rheum 32:974-983 (1989).

McCall MV, *A psychiatric perspective on insomnia*, J Clin Psychiatry 62(Suppl 10):27-32 (2001).

McCurry SM, Ancoli-Israel S, *Sleep dysfunction in Alzheimer's disease and other dementias* Curr Treat Options Neurol 5:261-272 (2003).

Nierenberg AA, Keefe BR, Leslie VC et al, *Residual symptoms in depressed patients who respond acutely to fluoxetine* J Clin Psychiatry 60:221-225 (1999).

Nolen, WA, *Hypnotics as concurrent medication in depression* Jrnl of Affective Disorders 28 (1993) 179-188.

O'Bryant SE, Palav A, McCaffrey RJ, *A review of symptoms commonly associated with menopause: implications for clinical neuropsychologists and other health care providers*, Neuropsychol Rev. 13:145-152 (2003).

Perlis ML, Giles DE, Buysse DJ, et al. *Self-reported sleep disturbance as a prodromal symptom in recurrent depression.* J Affect Disord 42:209-212 (1997).

Punjabi NM, Shahar E, Redline S, et al, Investigators SHHS, *Sleep-disordered breathing, glucose intolerance, and insulin resistance: the Sleep Heart Health Study* Am J Epidemiol 160:521-530 (2004).

Renko, A, Hiltunen L, Laakso M, et al. *The relationship of glucose tolerance to sleep disorders and daytime sleepiness* Diabetes Res Clin Pract 67:84-91 (2005).

Rickels K, Schweizer E, Case WG, DeMartinis N, Greenblatt DJ, Mandos LA, Espana FG. *Nefazodone in major depression: adjunctive benzodiazepine therapy and tolerability*, J, Clin Psychopharmacol 18:145-153 (1998).

Riemann D, Voderholzer U, *Primary Insomnia: a risk factor to develop depression*, J Affect Disord 76:255-259 (2003).

Shaver JL, *Women and sleep*, Nurse Clin North Am. 37:707-718 (2002).

Smith WT, Londborg PD, Glaudin V, Painter JR. *Shortterm augmentation of fluoxetine with clonazepam in the treatment of depression: a doub-blind study*, Am J. Psychiatry 155:1339-1345 (1998).

Smith WT, Londborg PD, Glaudin V, Painter JR. Summit Research Network. *Is extended clonazepam cotherapy of fluoxetine effective for outpatients with major depression?*, J Affect Disord 70:251-259 (2002).

Thorpy MJ, *Sleep disorders in Parkinson's disease* Clin Cornerstone 6 Suppl 1A:S7-15 (2004).

Tishler M, Barak Y, Paran D, Yaron M., *Sleep disturbances, fibromyalgia and primary Sjogren's syndrome* Clin Exp Rheumatol 15:71-74 (1997).

Van Cauter E, Polonsky KS, Scheen AJ, *Roles of circadian rhythmicity and sleep in human glucose regulation* Endocr Rev 18:716-738 (1997).

Walsh JK, *Clinical and socioeconomic correlates of insomnia*; J Clin Psychiatry 65 (Suppl 8):13-19 (2004).

Zamir G, Press J, Tal A, Tarasiuk A, *Sleep fragmentation in children with juvenile rheumatoid arthritis* J Rheumatol 25:1191-1197 (1998).

* cited by examiner

METHODS OF TREATMENT OF MENOPAUSE AND PERIMENOPAUSE USING ESZOPICLONE

CROSS REFERENCE TO RELATED APPLICATIONS

This application claims priority from U.S. provisional application 60/559,590, filed Apr. 5, 2004, the entire disclosure of which is incorporated herein by reference.

FIELD OF THE INVENTION

The invention relates to the use of eszopiclone for the treatment of menopause and perimenopause.

BACKGROUND OF THE INVENTION

Eszopiclone is a cyclopyrrolone that has the chemical name (+)6-(5-chloropyrid-2-yl)-5-(4-methylpiperazin-1-yl) carbonyloxy-7-oxo-6,7-dihydro-5H-pyrrolo[3-4-b]pyrazine or (+)6-(5-chloro-2-pyridinyl)-6,7-dihydro-7-oxo-5H-pyrrolo[3,4-b]pyrazin-5-yl 4-methylpiperazine-1-carboxylate. The chemical structure of eszopiclone is shown below:

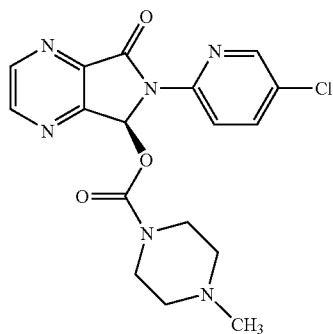

Eszopiclone is the S-(+)-optical isomer of the compound zopiclone, which is described in U.S. Pat. Nos. 6,319,926 and 6,444,673, and in Goa and Heel, [Drugs, 32:48-65 (1986)] and in U.S. Pat. Nos. 3,862,149 and 4,220,646. This isomer, which will hereinafter be referred to by its USAN-approved generic name, eszopiclone, includes the optically pure and the substantially optically pure (e.g., 90%, 95% or 99% optical purity) S-(+)-zopiclone isomer.

Zopiclone was the first of a chemically distinct class of hypnotic and anxiolytic compounds that offers a psychotherapeutic profile of efficacy and side effects similar to the benzodiazepines. This class of compounds, the cyclopyrrolones, appears to cause less residual sedation and less slowing of reaction times than the benzodiazepines, and it offers the promise of an improved therapeutic index over benzodiazepines.

The pharmacology of zopiclone has been shown both preclinically and clinically to be characterized by several elements. It is predominantly a hypnotic-sedative, offering significant activity on first treatment without concomitant respiratory or cardiac depression. The compound binds to the benzodiazepine receptor complex, or to a site linked closely to this receptor complex. (See Goa, K. L. and Heel, R. C. Drugs, 32:48-65, (1986); Brun, J. P., Pharmacology, Biochemistry and Behavior, 60 29:831-832, (1988); Julou, L. et al., Pharmacology, Biochemistry and Behavior, 23:653-659, (1985); Verma, A. and Snyder S. H., Ann. Rev. Pharmacol. Toxicol, 29:307-322, (1989). The central benzodiazepine receptor is a macromolecular complex that includes a site for the binding of gamma-aminobutyric acid (GABA), the inhibitory neurotransmitter, suggesting that benzodiazepines and chemically unrelated agonists including zopiclone may exert their effects by facilitating the synaptic effects of GABA. While it interacts with the benzodiazepine receptor, zopiclone apparently has minimal effects on memory, no interaction with alcohol, and little or no abuse or dependence potential. The drug is well absorbed from the stomach, and it is not highly bound to plasma proteins. The racemic mixture, zopiclone, has been in use for some years primarily as a hypnotic, and recently the USFDA approved use of eszopiclone (LUNESTRA™) for the treatment of insomnia.

SUMMARY OF THE INVENTION

The invention relates to methods of treating menopause and perimenopause with eszopiclone.

Thus, the invention relates to treating symptoms accompanying perimenopause or menopause comprising administering to a patient a therapeutically effective amount of eszopiclone.

DETAILED DESCRIPTION OF THE INVENTION

The invention relates to methods of treating menopause and perimenopause with eszopiclone. The S-(+)-zopiclone has an enantiomeric excess (e.e.) greater than 90%. It may be administered parenterally, transdermally or orally, preferably in an amount of 0.5 mg to 15 mg per day. In particular embodiments the eszopiclone is administered at 0.5 mg, 1.0 mg, 2.0 mg and 3.0 mg per day and in 0.5 mg, 1.0 mg, 2.0 mg and 3.0 mg per dosage.

It has now been discovered that Eszopiclone is useful for treating symptoms accompanying perimenopause or menopause. Menopause, which is caused by a lowering of the production of female sex hormones that typically occurs at around age 50, but can occur at much earlier or later ages, can generate disorders such as edema, hot flushes (or flashes), attacks of sweating, muscle and possibly joint pain, sleep disturbances, dysphoria, nervousness, mood swings, headache, palpitations (enhanced frequency of heart rate), dry mucous membranes, pain during intercourse and urinary disturbances. Hot flashes or flushing are characterized by a sudden onset of warmth in the face and neck, often progressing to the chest. Episodes generally last several minutes and are evidenced by a visible flushing of the skin. Often such episodes are accompanied by sweating, dizziness, nausea, palpitations and diaphoresis. Such symptoms can disrupt sleep and interfere with quality of life. Although the cause of hot flashes is not completely understood, they are thought to be a disorder of thermoregulation within the hypothalamus that is a consequence of declining estrogen levels. The administration of female sex hormones, such as estrogen, is effective in palliating these symptoms, but hormone therapy is fraught with undesirable side effects. Four out of five women have disturbing menopause disorders for at least one year and 25% of women have menopause disorders for more than 5 years. Half of all women have severe disorders. Men may also have hot flashes following androgen deprivation therapy (from bilateral orchiectomy or treatment with a gonadotrophin-releasing-hormone agonist) for metastatic prostate cancer. In view of this, it is apparent that there is a great need for safe compositions with a consistent efficacy for the treatment of disorders relating to hormonal variations in women during perimenopause and post menopause. Eszopiclone is particularly effective in decreasing nocturnal awakenings due to hot flashes and decreasing of overall perimenopausal or menopausal symptoms as demonstrated in clinical study presented in Example 1.

The pharmacologic profile of hypnotic-sedative, anxiolytic agents of the benzodiazepine class has been rather well established (Goodman and Gilman: The Pharmacological Basis of Therapeutics, 7th. Edition, Chapt. 17, 340-351, (1985), MacMillan Publishing Co., N.Y.) and has been extended to non-benzodiazepine agents of the cyclopyrrolone class (Bardone, M. C. et al., Abstract No. 2319, 7th. Int. Congr. Pharm. Paris, July, 1978, Pergamon Press, London; Julou, L. et al., Pharmacology, Biochemistry and Behavior, 23:653-659 (1985)). Accordingly, a variety of experimental models, which are rather well characterized (Julou, L. et al., ibid, 1985) can be used to characterize the various activities of eszopiclone. The acute toxicity of a pharmaceutical composition comprising zopiclone can be determined in studies in which rats are administered at progressively higher doses (mg/kg) of pharmaceutical composition. That lethal dose which, when administered orally, causes death of 50% of the test animals, is reported as the $LD_{50}$.

To establish the safety of eszopiclone, a dose escalation study was carried out. Cardiovascular and respiratory parameters were evaluated in conscious dogs following acute intravenous administration of (R)-, (S)- or racemic zopiclone at three doses (3, 5 and 12 mg/kg). Blood gases and blood chemistries (pH, pCO2, pO2, hematocrit, and lactate) remained unaffected in all dose groups. No evidence of cardiotoxicity, as evidence by the electrocardiogram (ECG), was observed following administration of racemic zopiclone or its enantiomers. Racemic zopiclone and eszopiclone produced dose dependent, transient decreases in blood pressure with an accompanying compensatory increase in heart rate, whereas (R) zopiclone had no effect. Administration of the highest dose (12 mg/kg) of racemic and (S)-zopiclone produced a more pronounced hypotensive effect (30-40% decrease from baseline). Complete recovery was not evident during the observational period. However, the values were returning toward baseline throughout the observation period. (R)-Zopiclone did not produce a consistent hemodynamic effect following 12 mg/kg.

Eszopiclone was evaluated for antimuscarinic activity in vivo. The racemate did not produce mydriasis in mice at any of the doses tested (maximum dose=100 mg/kg, p.o.). In another in vivo assay, neither (R)-, (S)-, nor racemic zopiclone significantly antagonized oxotremorine induced salivation in mice at doses up to 300 mg/kg, p.o. These results suggest that eszopiclone does not produce antimuscarinic effects and are consistent with eszopiclone's lack of in vitro affinity for muscarinic receptors.

All these studies point to little or no actions on the cardiovascular system or on the autonomic or peripheral nervous systems. Thus the drug appears to have a high safety margin with no indication of deleterious peripheral effects.

As used herein, and as would be understood by the person of skill in the medical art, to which the invention pertains, the recitation of the terms "eszopiclone" and "S-(+)-zopiclone" include pharmaceutically acceptable salts, hydrates, solvates, clathrates, and polymorphs of S-(+)-zopiclone. The term "pharmaceutically acceptable salt" refers to salts prepared from pharmaceutically acceptable non-toxic acids or bases including inorganic acids and bases and organic acids and bases. Salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. The term "solvate" refers to a compound—in this case eszopiclone—in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

The term "preventing" as used herein refers to administering a medicament beforehand to forestall or obtund an attack. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. The term "treating" includes prophylaxis as well as the amelioration of the acute symptoms. Note that "treating" refers to either or both of the amelioration of symptoms and the resolution of the underlying condition. The administration of eszopiclone may act not directly on the disease state, but rather on some pernicious symptom, and the improvement of that symptom leads to a general and desirable amelioration of the disease state.

As used herein, the recitation of the terms "eszopiclone" and "S-(+)-zopiclone" refers to eszopiclone having an enantiomeric excess (e.e.) greater than 90%. The term "enantiomeric excess" is well known in the art and is defined for a resolution of ab into a $$+b \text{ as } ee_a = \left(\frac{\text{conc. of } a - \text{conc. of } b}{\text{conc. of } a + \text{conc. of } b}\right) \times 100$$

The term "enantiomeric excess" is related to the older term "optical purity" in that both are measures of the same phenomenon. The value of ee will be a number from 0 to 100, zero being racemic and 100 being pure, single enantiomer. A compound which in the past might have been called 98% optically pure is now more precisely described as 96% ee.; in other words, a 90% e.e. reflects the presence of 95% of one enantiomer and 5% of the other in the material in question. In the case of eszopiclone, e.e. of greater than 95% is preferred; e.e. of greater than 98% is more preferred; and e.e. of greater than 99% is most preferred.

Racemic zopiclone is commercially available and can be made using various methods, such as those disclosed in U.S. Pat. Nos. 3,862,149 and 4,220,646. Eszopiclone is also commercially available or it may be prepared from racemic zopiclone using standard methods, such as chiral-phase chromatography, resolution of an optically active salt, stereoselective enzymatic catalysis by means of an appropriate microorganism, or asymmetric synthesis. U.S. Pat. No. 6,319,926 discloses methods for making (+) zopiclone, including resolution from racemic zopiclone by means of an optically active acid, such as D(+)-O,O'-dibenzoyltartaric acid.

Another method for making Eszopiclone is by synthesis from racemic zopiclone (or (RS)-zopiclone) by chemical resolution via the D-malate salt as shown in the following synthesis schematic.

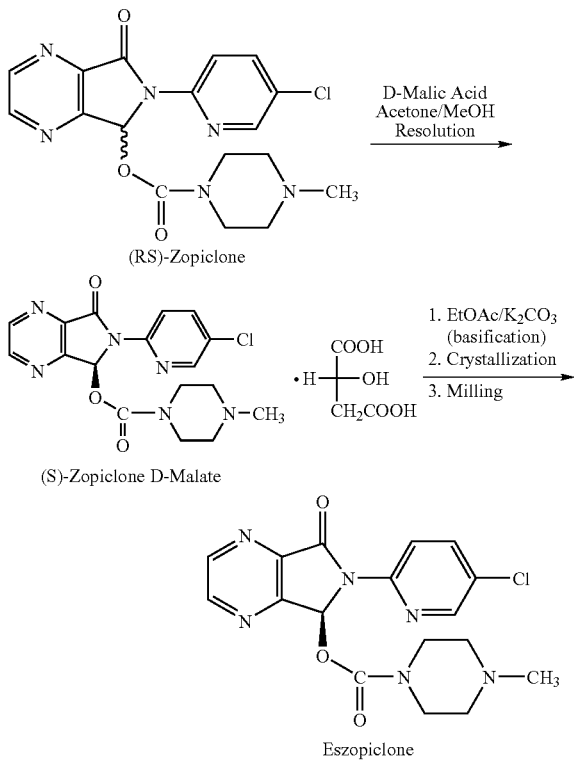

In the synthetic route shown above, (RS)-zopiclone and D-malic acid are dissolved in a mixture of acetone and methanol to form (S)-zopiclone D-malate and (R)-zopiclone D-malate. The two diastereomeric salts are resolved in-situ by selective crystallization, filtration and rinsing to produce highly (S)-enriched zopiclone D-malate salt. In this process, the majority of (R)-zopiclone D-malate remains in the mother liquors. In this method, the use of an acetone/methanol co-solvent system results in a highly diastereoselective salt crystallization, and preferably, the co-solvent ratio used should be in the range of approximately 1.9/1 to 2.3/1 w/w acetone in methanol. Preferably, this stage of the process may also include cooling the reaction mixture during the isolation step to a temperature in the inclusive range of about 10° C. to 15° C., and washing or rinsing the wet cake obtained after filtration with cold solvent, such as cold methanol.

The resulting (S)-zopiclone D-malate salt is converted to optically pure (S)-zopiclone free base by treatment with aqueous potassium carbonate and ethyl acetate, followed by phase separation and crystallization. In this process, once a solution of (S)-zopiclone free-base is obtained, additional enantiomeric enrichment (typically 1 to 4%) can be achieved by crystallization from ethyl acetate of low water content. The water content can be controlled, e.g., by azeotropic distillation, and incorporating an in-process control of water content into the crystallization process can further improve the robustness of enantiomeric purity. Preferably, the water level during this step is 2% or less, more preferably 1% or less, and most preferably 0.6% or less. The resulting optically pure eszopiclone free base can then be milled to a desired size for use as an active ingredient in a pharmaceutical composition according to the present invention. These compositions are useful in treating disorders that are affected by the binding of agonists to central nervous system and peripheral benzodiazepine receptors while avoiding the adverse effects associated with the administration of the racemic mixture of zopiclone.

The size of a prophylactic or therapeutic dose of eszopiclone in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 0.5 mg to about 15 mg. Preferably, a daily dose range should be between about 0.5 mg to about 12.5 mg. Most preferably, a daily dose range should be between about 2.0 mg to about 10.0 mg. In managing the patient, the therapy may be initiated at a lower dose, perhaps about 0.5 mg to about 7.5 mg and increased up to about 10 mg or higher depending-on the patient's global response. It is further recommended that children and patients over 65 years, and those with impaired renal or hepatic function, initially receive low doses, and that they be titrated based on global response and blood level. It may be necessary to use dosages outside these ranges in some cases.

Pharmaceutical compositions of the present invention may be administered by any suitable route of administration that provides a patient with a therapeutically effective dosage of eszopiclone. Typically, the eszopiclone pharmaceutical compositions described herein will be formulated for oral administration or for inhalation. Suitable dosage forms include tablets, troches, cachets, caplets, capsules, including hard and soft gelatin capsules, and the like. Tablet forms, however, remain a preferred dosage form because of advantages afforded both the patient (e.g., accuracy of dosage, compactness, portability, blandness of taste and ease of administration) and to the manufacturer (e.g., simplicity and economy of preparation, stability and convenience in packaging, shipping and dispensing).

The pharmaceutical compositions may further include a "pharmaceutically acceptable inert carrier" and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques. In one embodiment, coating with hydroxypropylmethylcellulose (HPMC) is employed. "Pharmaceutically acceptable carrier" also encompasses controlled release means. Compositions of the present invention may also optionally include other therapeutic ingredients, anti-caking agents, preservatives, sweetening agents, colorants, flavors, desiccants, plasticizers, dyes, and the like. However, any such optional ingredient must be compatible with eszopiclone to insure the stability of the formulation.

In the case where an oral composition is employed, a suitable dosage range for use is from about 0.5 mg to about 15.0 mg. Preferably, a dose range of between about 0.5 mg to about 12.5 mg is given as a once daily administration or in divided doses if required; most preferably, a dose range of from about 0.5 mg to about 10 mg is given, either as a once daily administration or in divided doses if required. Patients may be upward titrated from below to within this dose range to a satisfactory control of symptoms as appropriate.

Capsule Formulation

| ingredient | mg per capsule formulation A | mg per capsule formulation B | mg per capsule formulation C | mg per capsule formulation D |
|---|---|---|---|---|
| Eszopiclone | 0.5 | 1.0 | 2.0 | 3.0 |
| lactose | 79 | 78.5 | 77.5 | 76.5 |
| corn starch | 20 | 20 | 20 | 20 |
| magnesium stearate | 0.5 | 0.5 | 0.5 | 0.5 |
| total weight | 100 | 100 | 100 | 100 |

The active ingredient, eszopiclone, lactose, and corn starch are blended until uniform; then the magnesium stearate is blended into the resulting powder. The resulting mixture is encapsulated into suitably sized two-piece hard gelatin capsules.

Tablet Formulation

| ingredient | mg per tablet formulation A | mg per tablet formulation B | mg per tablet formulation C | mg per tablet formulation D |
|---|---|---|---|---|
| Eszopiclone | 0.5 | 1.0 | 2.0 | 3.0 |
| lactose | 153 | 152.5 | 151.5 | 150.5 |
| corn starch | 30 | 30 | 30 | 30 |
| pre-gelatinized corn starch | 15 | 15 | 15 | 15 |
| magnesium stearate | 1.5 | 1.5 | 1.5 | 1.5 |
| compression weight | 200 | 200 | 200 | 200 |

The active ingredient, eszopiclone, is sieved through a suitable sieve and blended with lactose, starch, and pregelatinized cornstarch. Suitable volumes of purified water are added and the powders are granulated. After drying, the granules are screened and blended with the magnesium stearate. The granules are then compressed into tablets using 7 mm diameter punches.

Tablets of other strengths may be prepared by altering the ratio of active ingredient to lactose or the compression weight and using punches to suit. In one embodiment, eszopiclone is formulated as film-coated tablets for oral administration containing the following inactive ingredients: calcium phosphate, colloidal silicon dioxide, croscarmellose sodium, hypromellose, lactose, magnesium stearate, microcrystalline cellulose, polyethylene glycol, titanium dioxide, triacetin and optionally FD&C Blue #2.

EXAMPLE 1

Clinical Study on Treatment of Menopause or Perimenopause with Eszopiclone

The study was aimed at observing efficacy of eszopiclone 3 mg compared to placebo in the treatment of insomnia secondary to perimenopause or menopause. The study was a multicenter, randomized, double-blind, placebo-controlled, parallel-group study. The study had a one-week single-blind placebo run-in period, followed by four weeks of double blind treatment, and one week of single blind placebo washout. The primary method of analysis compared the post-randomization results between the two treatment groups.

Subjects were women with insomnia secondary to perimenopause or menopause. Subjects were perimenopausal or menopausal and had insomnia symptoms including $\geq 45$ minutes sleep latency (SL) and total sleep time (TST) $\leq 6$ hours. Perimenopausal/menopausal symptoms predated the onset of sleep disturbance symptoms. The patient population was predominately Caucasian (77.2%). The mean age was 49, with a range of 40-60.

A total of 410 subjects were randomized. Among them, 201 received 3 mg of eszopiclone (ESZ) nightly (at bedtime) for four weeks and 209 received matching placebo (PBO). The discontinuation rates were moderate, 11.9% in the ESZ group and 12.9% in the PBO group.

The ESZ group had significantly fewer nocturnal awakenings due to hot flashes during Week 1 compared with PBO (LS means of 0.3 and 0.5 per night for ESZ and PBO, respectively; p=0.0016). This effect was not significant for the other weeks, but was marginally significant for the DB average (p=0.059). When change from baseline was analyzed, ESZ significantly reduced the number of nocturnal awakenings due to hot flashes in Week 1 compared with PBO (p<0.0001). The difference was not significant for Week 2, but was marginally significant for Weeks 3 and 4 (p=0.094 and 0.055, respectively) and was significant for the DB average (p=0.0045). See Table 1.

TABLE 1

Number of Nocturnal Awakenings due to Hot Flashes (Intent-to-Treat Population)

| Time Point | Statistic | Placebo Observed Value | Placebo Change from Baseline [1] | Eszopiclone 3 mg Observed Value | Eszopiclone 3 mg Change from Baseline [1] |
|---|---|---|---|---|---|
| Baseline | N | 171 | | 150 | |
| | Mean (SD) | 1.1 (1.2) | | 1.3 (1.2) | |
| | 25th Percentile | 0.0 | | 0.3 | |
| | Median | 1.0 | | 1.0 | |
| | 75th Percentile | 1.5 | | 2.0 | |
| | Minimum, Maximum | 0.0, 10.0 | | 0.0, 6.0 | |
| Week 1 | N | 179 | 157 | 175 | 140 |
| | Mean (SD) | 0.8 (1.0) | −0.2 (0.9) | 0.5 (0.7) | −0.7 (1.0) |
| | 25th Percentile | 0.0 | −0.7 | 0.0 | −1.2 |
| | Median | 0.5 | 0.0 | 0.2 | −0.5 |
| | 75th Percentile | 1.3 | 0.2 | 1.0 | 0.0 |
| | Minimum, Maximum | 0.0, 5.0 | −5.0, 2.3 | 0.0, 3.0 | −6.0, 0.8 |
| | Least Squares Means (SE) [2] | 0.8 (0.1) | | 0.5 (0.1) | |
| | p-value vs. placebo [2] | | | <.0001 | |
| | Least Squares Means (SE) [3] | | −0.3 (0.1) | | −0.7 (0.1) |
| | p-value vs. placebo [3] | | | | <.0001 |
| Week 2 | N | 174 | 153 | 170 | 139 |
| | Mean (SD) | 0.6 (0.8) | −0.5 (1.0) | 0.5 (0.7) | −0.7 (0.7) |
| | 25th Percentile | 0.0 | −1.0 | 0.0 | −1.0 |
| | Median | 0.3 | −0.4 | 0.0 | −0.6 |
| | 75th Percentile | 1.0 | 0.0 | 1.0 | 0.0 |
| | Minimum, Maximum | 0.0, 4.3 | −6.8, 1.3 | 0.0, 3.0 | −6.0, 2.0 |

TABLE 1-continued

Number of Nocturnal Awakenings due to Hot Flashes (Intent-to-Treat Population)

| Time Point | Statistic | Placebo Observed Value | Placebo Change from Baseline [1] | Eszopiclone 3 mg Observed Value | Eszopiclone 3 mg Change from Baseline [1] |
|---|---|---|---|---|---|
| | Least Squares Means (SE) [2] | 0.6 (0.1) | | 0.5 (0.1) | |
| | p-value vs. placebo [2] | | | 0.2137 | |
| | Least Squares Means (SE) [3] | | −0.5 (0.1) | | −0.6 (0.1) |
| | p-value vs. placebo [3] | | | | 0.1963 |
| Week 3 | N | 162 | 147 | 164 | 129 |
| | Mean (SD) | 0.6 (0.8) | −0.5 (1.0) | 0.5 (0.7) | −0.7 (1.1) |
| | 25th Percentile | 0.0 | −0.8 | 0.0 | −1.0 |
| | Median | 0.3 | −0.3 | 0.0 | −0.4 |
| | 75th Percentile | 1.0 | 0.0 | 1.0 | 0.0 |
| | Minimum, Maximum | 0.0, 4.6 | −6.2, 2.7 | 0.0, 3.0 | −6.0, 1.5 |
| | Least Squares Means (SE) [2] | 0.6 (0.1) | | 0.5 (0.1) | |
| | p-value vs. placebo [2] | | | 0.1583 | |
| | Least Squares Means (SE) [3] | | −0.5 (0.1) | | −0.6 (0.1) |
| | p-value vs. placebo [3] | | | | 0.2408 |
| Week 4 | N | 151 | 135 | 154 | 121 |
| | Mean (SD) | 0.6 (0.9) | −0.5 (1.0) | 0.4 (0.7) | −0.8 (1.2) |
| | 25th Percentile | 0.0 | −1.0 | 0.0 | −1.3 |
| | Median | 0.0 | −0.3 | 0.0 | −0.7 |
| | 75th Percentile | 1.0 | 0.0 | 1.0 | 0.0 |
| | Minimum, Maximum | 0.0, 5.3 | −4.8, 4.0 | 0.0, 3.6 | −6.0, 2.1 |
| | Least Squares Means (SE) [2] | 0.6 (0.1) | | 0.4 (0.1) | |
| | p-value vs. placebo [2] | | | 0.0786 | |
| | Least Squares Means (SE) [3] | | −0.5 (0.1) | | −0.7 (0.1) |
| | p-value vs. placebo [3] | | | | 0.0683 |
| DB Average | N | 192 | 165 | 188 | 146 |
| | Mean (SD) | 0.7 (0.8) | −0.4 (0.9) | 0.5 (0.6) | −0.7 (1.0) |
| | 25th Percentile | 0.0 | −0.8 | 0.0 | −1.1 |
| | Median | 0.4 | −0.2 | 0.2 | −0.5 |
| | 75th Percentile | 1.0 | 0.0 | 0.9 | 0.0 |
| | Minimum, Maximum | 0.0, 4.6 | −6.0, 1.5 | 0.0, 2.7 | −6.0, 1.5 |
| | Least Squares Means (SE) [2] | 0.7 (0.1) | | 0.5 (0.1) | |
| | p-value vs. placebo [2] | | | 0.0057 | |
| | Least Squares Means (SE) [3] | | −0.4 (0.0) | | −0.7 (0.1) |
| | p-value vs. placebo [3] | | | | 0.0016 |

[1] Week 1 = First week of double-blind treatment, Week 2 = Second week of double-blind treatment, etc. DB Average includes all scheduled assessments obtained after Visit 3 up to and including Visit 5. Baseline is the average of all pre-DB observations.
[2] The pairwise comparison is a two-sided test performed using an ANOVA model, using the MIXED procedure with treatment and site as fixed effects.
[3] The pairwise comparison is a two-sided test performed using an ANCOVA model, using the MIXED procedure with treatment and site as fixed effects and baseline as the covariate.

A Physician Global Assessment was administered at Week 4, the end of the double-blind treatment period. ESZ patients had significantly better scores at this time compared with PBO (LS means of 2.7 and 3.3 for ESZ and PBO, respectively; $p<0.0001$). See Table 2.

TABLE 2

Menopause and Perimenopause Study, Physician Global Assessment (Intent-to-Treat Population)

| Visit (Week) | Statistic | Placebo Observed Value | Placebo Change from Baseline | Eszopiclone 3 mg Observed Value | Eszopiclone 3 mg Change from Baseline |
|---|---|---|---|---|---|
| 3 (Baseline) | N | 202 | | 195 | |
| | Mean (SD) | 3.6 (1.0) | | 3.7 (1.0) | |
| | 25th Percentile | 3.0 | | 4.0 | |
| | Median | 4.0 | | 4.0 | |
| | 75th Percentile | 4.0 | | 4.0 | |
| | Minimum, Maximum | 0.0, 6.0 | | 0.0, 7.0 | |
| 5 (Week 4) | N | 191 | 188 | 189 | 185 |
| | Mean (SD) | 3.3 (1.1) | −0.3 (1.4) | 2.6 (1.2) | −1.0 (1.4) |
| | 25th Percentile | 2.0 | −1.0 | 2.0 | −2.0 |
| | Median | 4.0 | 0.0 | 2.0 | −1.0 |
| | 75th Percentile | 4.0 | 0.0 | 4.0 | 0.0 |
| | Minimum, Maximum | 1.0, 6.0 | −4.0, 5.0 | 1.0, 6.0 | −4.0, 6.0 |
| | Least Squares Means (SE) [1] | 3.3 (0.1) | | 2.7 (0.1) | |
| | p-value vs. placebo [1] | | | <.0001 | |
| | Least Squares Means (SE) [2] | | −0.3 (0.1) | | −0.9 (0.1) |
| | p-value vs. placebo [2] | | | | <.0001 |

[1] The pairwise comparison is a two-sided test performed using an ANOVA model, using the MIXED procedure with treatment and site as fixed effects.
[2] The pairwise comparison is a two-sided test performed using an ANCOVA model, using the MIXED procedure with treatment and site as fixed effects and baseline as the covariate.
Note(s):
The responses to the assessment question: Overall the subject's perimenopausal or menopausal symptoms since the last assessment are: 0 = Not assessed, 1 = Very much improved, 2 = Much improved, 3 = Minimally improved, 4 = No change, 5 = Minimally worse, 6 = Much worse, 7 = Very much worse.

The results of the study will change slightly because data from one site, consisting of 11 of the 410 subjects analyzed above will be excluded due to negative findings during a site audit. It is expected that the conclusions of the study will not change after exclusion of these 11 subjects.

The contents of each of the references cited herein, including the contents of the references cited within the primary references, are herein incorporated by reference in their entirety. The invention being thus described, it is apparent that the same can be varied in many ways. Such variations are not to be regarded as a departure from the spirit and scope of the present invention, and all such modifications and equivalents as would be obvious to one skilled in the art are intended to be included within the scope of the following claims.

The invention claimed is:

1. A method for treating hot flashes accompanying perimenopause or menopause in a patient having perimenopause or menopause symptoms, the method comprising administering to the patient having perimenopause or menopause symptoms a therapeutically effective amount of eszopiclone having an enantiomeric excess greater than ninety percent.

2. A method according to claim 1 wherein said eszopiclone is administered parenterally, transdermally, orally or by inhalation.

3. A method according to claim 1 wherein said eszopiclone is administered in an amount of 0.5 mg to 15 mg per day.

4. A method according to claim 3 wherein said eszopiclone is administered in an amount chosen from of 0.5 mg, 1.0 mg, 2.0 mg and 3.0 mg per dosage.

* * * * *